(12) United States Patent
DelSignore

(10) Patent No.: US 9,707,090 B2
(45) Date of Patent: Jul. 18, 2017

(54) SURGICAL IMPLANTABLE STABILIZER SLING FOR BASAL JOINT ARTHROPLASTY

(71) Applicant: Jeanne L. DelSignore, Rochester, NY (US)

(72) Inventor: Jeanne L. DelSignore, Rochester, NY (US)

(73) Assignee: CMC Group LLC, Newton, MA (US)

( * ) Notice: Subject to any disclaimer, the term of this patent is extended or adjusted under 35 U.S.C. 154(b) by 0 days.

(21) Appl. No.: 14/602,548

(22) Filed: Jan. 22, 2015

(65) Prior Publication Data

US 2015/0366672 A1 Dec. 24, 2015

Related U.S. Application Data

(63) Continuation of application No. 12/577,057, filed on Oct. 9, 2009, now abandoned.

(60) Provisional application No. 61/197,060, filed on Oct. 23, 2008.

(51) Int. Cl.
| | | |
|---|---|---|
| A61F 2/42 | (2006.01) | |
| A61B 17/04 | (2006.01) | |
| A61B 17/82 | (2006.01) | |
| A61F 2/08 | (2006.01) | |
| A61B 17/06 | (2006.01) | |

(52) U.S. Cl.
CPC ........ *A61F 2/4241* (2013.01); *A61B 17/0401* (2013.01); *A61B 17/06066* (2013.01); *A61B 17/06166* (2013.01); *A61B 17/82* (2013.01); *A61F 2/08* (2013.01); *A61F 2/0811* (2013.01); *A61B 17/826* (2013.01); *A61B 2017/0427* (2013.01); *A61B 2017/0464* (2013.01); *A61F 2002/4253* (2013.01)

(58) Field of Classification Search
CPC .......... A61B 17/0401; A61B 17/06066; A61B 17/06166; A61B 2017/0427; A61F 2/4241; A61F 2/0811; A61F 2002/4253
See application file for complete search history.

(56) References Cited

U.S. PATENT DOCUMENTS

| | | |
|---|---|---|
| 3,496,940 A | 2/1970 | Steinman |
| 3,545,008 A | 12/1970 | Bader, Jr. |
| 3,745,590 A | 7/1973 | Stubstad |
| 3,805,300 A | 4/1974 | Tascon-Alonso et al. |
| 4,187,558 A | 2/1980 | Dahlen et al. |
| 4,713,075 A | 12/1987 | Kurland |
| 4,775,380 A | 10/1988 | Seedhom et al. |

(Continued)

FOREIGN PATENT DOCUMENTS

| | | |
|---|---|---|
| WO | WO 2006/034719 | 4/2006 |
| WO | WO 2007/002071 | 1/2007 |
| WO | WO 2010/047981 | 4/2010 |

OTHER PUBLICATIONS

Updated 510(k) Sterility Review Guidance K90-1; Guidance for Industry and FDA, Aug. 30, 2002, pp. 1-6.*
Badia, Alejandro, Surgical Options for Thumb Basal Joint Arthritis, US Musculoskeletal Review, 2006, pp. 69-70.
Cassidy et al., Basal Joint Arthoplasty and Carpal Tunnel Release Through a Single Incision: An In Vitro Study, J. Hand Surg., vol. 29A, pp. 1085-1088.

(Continued)

*Primary Examiner* — Brian Dukert
(74) *Attorney, Agent, or Firm* — Pandiscio & Pandiscio

(57) ABSTRACT

The concepts disclosed herein offer a new simple and reliable reconstructive option for the treatment of first carpal-metacarpal joint (basal joint) arthritis and consists of an intra-articular basal joint stabilizer sling combined with a surgical method of implantation.

14 Claims, 6 Drawing Sheets

(56) References Cited

U.S. PATENT DOCUMENTS

| | | |
|---|---|---|
| 5,702,468 A | 12/1997 | Goldberg |
| 5,860,978 A | 1/1999 | McDevitt et al. |
| 6,010,447 A | 1/2000 | Kardjian |
| 6,042,534 A | 3/2000 | Gellman et al. |
| 6,110,101 A | 8/2000 | Tihon et al. |
| 6,368,326 B1 | 4/2002 | Dakin et al. |
| 6,517,578 B2 | 2/2003 | Hein |
| 6,872,227 B2 | 3/2005 | Sump et al. |
| 7,083,568 B2 | 8/2006 | Neisz et al. |
| 8,460,319 B2 | 6/2013 | Wales et al. |
| 2002/0019670 A1 | 2/2002 | Crawley et al. |
| 2002/0123750 A1 | 9/2002 | Eisermann et al. |
| 2003/0139775 A1 | 7/2003 | Grafton |
| 2004/0127906 A1 | 7/2004 | Culbert et al. |
| 2005/0019368 A1 | 1/2005 | Cook et al. |
| 2006/0149261 A1 | 7/2006 | Nilsson et al. |
| 2006/0195007 A1 | 8/2006 | Anderson et al. |
| 2006/0241617 A1 | 10/2006 | Holloway et al. |
| 2009/0018655 A1* | 1/2009 | Brunelle .......... A61L 27/24 623/13.19 |
| 2009/0171143 A1 | 7/2009 | Chu et al. |
| 2009/0254190 A1 | 10/2009 | Gannoe et al. |
| 2009/0306776 A1 | 12/2009 | Murray |
| 2011/0208239 A1 | 8/2011 | Stone et al. |
| 2013/0211451 A1 | 8/2013 | Wales et al. |

OTHER PUBLICATIONS

Delsignore et al., Suture Suspension Arthoplasty Technique for Basal Joint Arthritis Reconstruction, Techniques in Hand and Upper Extremity, to be published, Dec. 2009.

Delsignore, Jeanne, A Modified Technique for Basal Joint Suspensionplasty, Am. Soc. Hand Surgery, Aug. 2004, Issue No. 52.

Glickel et al.; Basal Joint Arthroplasty: Indications and Treatment, Current Opinion in Orthopaedics, 2001, vol. 12, pp. 290-292.

Griggs et al., The Use of Suture Anchors in the Hand and Wrist, in Current Practice in Hand Surgery, 1997, pp. 73-77, Mosby, St. Louis/USA.

Heyworth, Benton, Tendon Transfer Arthoplasy vs. LRTI Arthoplasty . . . , Doris Duke Medical Student's Journal, vol. II, 2002-2003, pp. 46-52.

Matullo et al., CMC Arthroplasty of he Thumb: A Review, Am. Assn. Hand Surgery, Aug. 7, 2007.

PCT Search Report for PCT Application No. PCT/US2009/060263; mailed Dec. 1, 2009; 3 pages.

Shaieb et al., Tensile Strengths of Various Suture Techniques, J. Hand Surgery (British and European Volume, 1997), vol. 22B, pp. 764-767.

Shuler et al., Basal Joint Arthritis of the Thumb, J. Am. Acad. Orthop. Surg., 2008 vol. 16, pp. 418-423.

Weidrich et al., The Use of Suture Anchors in the Hand and Wrist, Operative Tech. in Plastic and Recon. Surg., 1997, vol. 4, pp. 42-48.

\* cited by examiner

Basal Joint Stablizer Sling

Suture Anchor Detail

SIDE VIEW

SIDE VIEW
Rotated Axially 90°

WOVEN SLING
PLAN VIEW

WOVEN SLING
SIDE VIEW

SLING ATTACHMENT
VIA
SUTURES and BONE ANCHOR

ALTERNATIVE SLING CONFIGURATION

ALTERNATIVE SLING IMPLANTATION

ALTERNATIVE SLING CONFIGURATION

ALTERNATIVE SLING IMPLANTATION

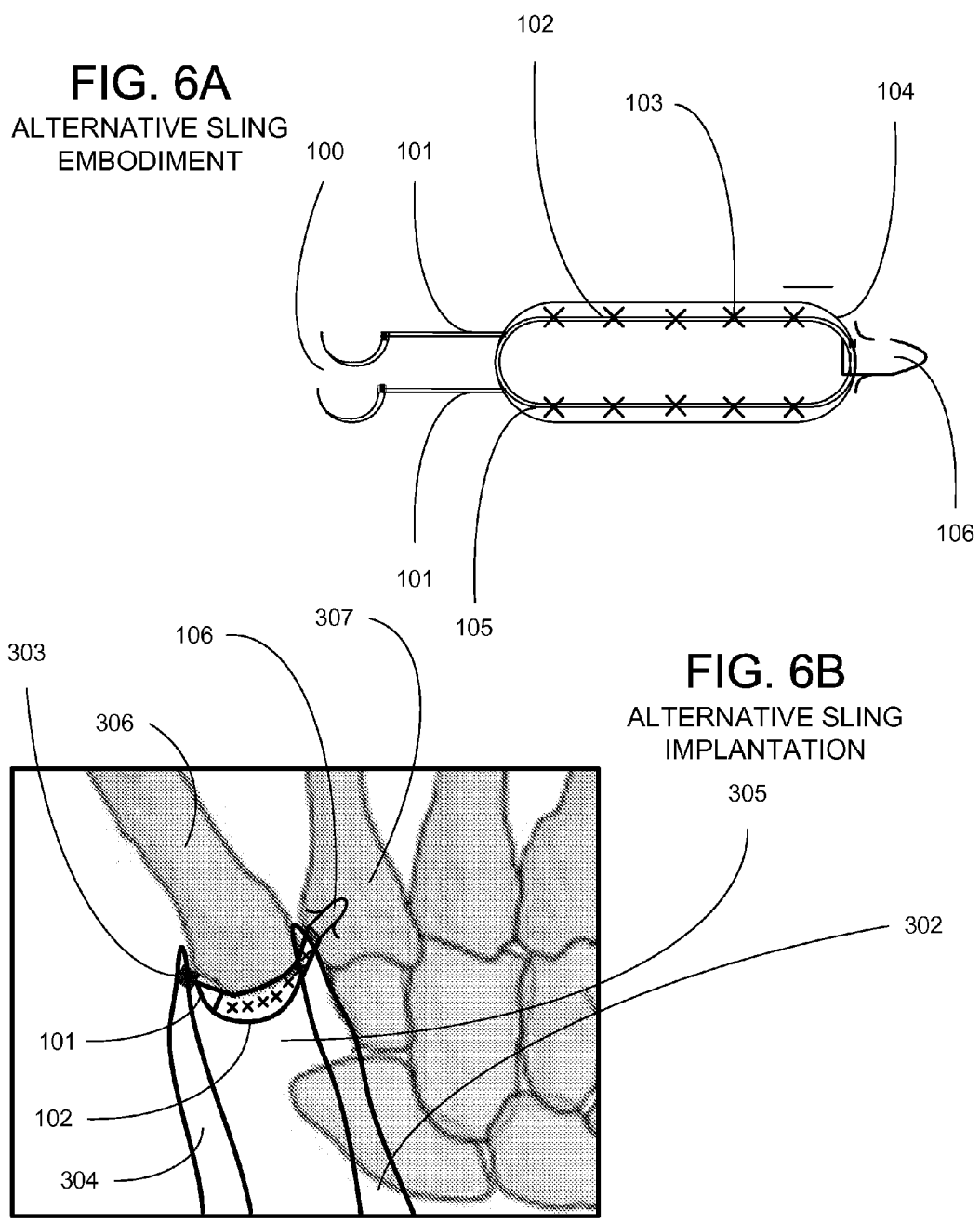

SURGICAL IMPLANTABLE STABILIZER SLING FOR BASAL JOINT ARTHROPLASTY

REFERENCE TO PENDING PRIOR PATENT APPLICATIONS

This patent application is a continuation of pending prior U.S. patent application Ser. No. 12/577,057, filed Oct. 9, 2009 by Jeanne L. DelSignore for A SURGICAL IMPLANTABLE STABILIZER SLING FOR BASAL JOINT ARTHROPLASTY, which in turn claims benefit of prior U.S. Provisional Patent Application Ser. No. 61/197,060, filed Oct. 23, 2008 by Jeanne Louise DelSignore for SURGICAL IMPLANTABLE STABILIZER SLING FOR BASAL JOINT ARTHROPLASTY.

The above-identified patent applications are hereby incorporated herein by reference.

FIELD OF THE INVENTION

This application relates to an implantable stabilizer sling for the surgical repair and reconstruction of joints, preferably of the hands, in particular the basal joint.

BACKGROUND OF THE INVENTION

Degenerative osteoarthritis of the first carpal-metacarpal joint (basal joint) of the thumb is a common, disabling condition, especially in middle-aged women. Investigations show that about 25% of all women and 8% of men in their fifties complain of pain at the base of the thumb, secondary to osteoarthritis. This condition causes joint instability and subluxation, due to incompetence of an important stabilizing structure, the volar oblique ligament, resulting in dorsal subluxation, adduction contracture, and subsequent compensatory metacarpal-phalangeal joint hyperextension deformity. As arthritis progresses, patients suffer from load-related pain, affecting pinching and gripping activities, and experience weakness, severe dysfunction, reduced mobility, and loss of functionality. Several methods of basal joint reconstruction have been proposed, most of which involve some form of soft tissue reconstruction which have historically involved harvesting tendons which are subsequently transferred and re-directed via drill holes in the thumb metacarpal to restore proper balance, alignment, and prevent cantilever displacement forces at the base of the thumb. These methods involve harvesting and thereby sacrificing an entire or a portion of a functioning tendon, which is utilized to create a suspension and stabilization of the basal joint. Many of the past described surgical methods require temporary pin fixation of the joint, subsequent pin removal and have been associated with pin tract complications, such as infection, nerve damage, neuroma formation, and these methods which utilize more extensive and often multiple incisions cause increased surgical morbidity. One method simply involves removing the arthritic articulation by excising the trapezium and temporarily pinning the joint in distraction. This procedure can provide pain relief, but is associated with persistent collapse deformity, proximal migration, and weakness. The key principles of successful basal joint arthroplasty involve trapezial excision, which is required for pain relief, and some form of ligament reconstruction, which restores the function of the important volar stabilizing ligament, thereby re-creating the proper balance, alignment, longitudinal length, and function of the thumb. With ligament reconstruction, not only is pain relief attained but strength, alignment and stability are achieved.

Several methods of artificial joint replacement have been utilized including those made of silicone, metal/plastic with cemented or non-cemented implants, and more recently, synthetic fabrics for interposition. Each of these methods have had significant failure rates and complications related to implant failure, fracture of the bone interfaces, particulate synovitis, dislocation and loss of stability over time. Revision rates have been high with the prosthetic implants, most of which have not addressed the concept of ligamentous reconstruction and re-creation of the important function of the volar oblique ligament, which appears to be essential for restoring proper balance and function to the reconstructed basal joint. Additional problems with the recently developed synthetic fabric inserted into the basal joint include irritation over the synthetic fabric, which is secured to the dorsal base of the thumb metacarpal, potential fixation problems, as well as the fact that the synthetic fabric design only addresses the distal articular surface of the basal joint, leaving the proximal joint (scaphoid-trapezial joint) interface intact. This particular form of synthetic implant is limited in use for patients with very early arthritis, involving only the distal carpal-metacarpal joint and is not appropriate for the larger cohort of arthritic patients who suffer from arthritis in a more extensive, pan-trapezial (surrounding the trapezium on all articular surfaces) fashion.

The various techniques employed in basal joint arthroplasty have recently been the subject of discussion in several medical journals. "Basal Joint Arthritis of the Thumb" has been reviewed by Michael S. Shuler, Shai Luria, and Thomas E. Trumble in the Journal of the American Academy of Orthopaedic Surgeons 2008; 16: 418-423, which is hereby incorporated by reference. "CMC Arthroplasty of the Thumb: A Review" has been reviewed by Kristofer S. Matullo, Asif Hyas, and Joseph J. Thoder in Hand (2007) 2: 232-239, which is hereby incorporated by reference. "Basal Joint Arthroplasty: Indications and Treatment" has been reviewed by Steven Z. Glickel and Landon T. Home in Current Opinion in Orthopaedics 2001, 12: 290-294, which is hereby incorporated by reference.

One of the methods frequently utilized, the Ligament Reconstruction, Tendon Interposition technique, (LRTI) involves sacrificing the flexor carpi radialis tendon, either in whole or in part. This technique requires one or two additional forearm incisions to harvest a wrist flexor tendon, formation of a drill hole within the metacarpal base to re-direct the tendon reconstruction, rolling up the remaining tendon which is placed into the arthroplasty space, pinning the joint for 4-6 weeks, and immobilization in a post-operative cast for 4-6 weeks, after which thumb/wrist orthotics are utilized and hand therapy is instituted for 2-3 months. Typical return to normal activities can be expected in about 6 months to a year. Long term results have been excellent with regard to pain relief, but the healing process is lengthy, incisions are extensive and multiple, subsidence with loss of arthroplasty space has been reported, pin tract complications do occur, aid the technique is technically demanding, lengthy and requires sacrificing a normal, functioning wrist flexor tendon.

One method for treatment of basal joint arthritis is a simple excision of the trapezium and pinning the joint in slight distraction with the pin removed at 4-6 weeks post-operative. This technique does not address ligament reconstruction to restore function of the incompetent volar oblique ligament, and includes the disadvantages and risks of pin fixation. Collapse of resection arthroplasty space (subsidence), persistent dorsal subluxation, persistent adduction contracture, and compensatory metacarpal-phalangeal joint hyperextension deformity is common, but pain relief is reported to be satisfactory. This technique may not be appropriate for younger, higher demand patients.

Another method for soft tissue reconstruction that has been disclosed in the American Society for Surgery of the Hand Correspondence Newsletter, 2004-52, DelSignore, August, 2004, which is hereby incorporated by reference, involves a modification of the Weilby technique, by utilizing an ulnarly based slip of the abductor pollicis longus tendon, and avoids the need for drill holes to redirect the tendon, avoids the need for pin fixation, and requires only 4 weeks of cast immobilization, with typical return to heavy manual activities for the majority of patients at 3 months (12 weeks) post operative. This technique utilizes only one distally based slip of the abductor pollicis longus tendon which does not sacrifice it's function, but does require an incision that extends proximal to the wrist flexion crease and can be associated with some residual wrist stiffness, as wrist immobilization is recommended for four weeks post-operatively which can result in a longer period of recovery of wrist and hand motion. Patients may experience some temporary and rarely permanent irritation of the dorsal sensory branch of the radial nerve, as the incision does cross the wrist flexion crease in a proximal and radial direction, requiring very careful identification and retraction of branches of the nerve.

A surgical method developed by the author of this patent application is disclosed in *Suture Suspension Arthroplasty Technique for Basal Joint Arthritis Reconstruction*, DelSignore and Accardi, to be published in Techniques in Hand and Upper Extremity, December, 2009, which is hereby incorporated by reference. This novel technique avoids tendon harvesting altogether and provides the distinct advantage of utilizing a single small incision (Wagner), which does not cross the wrist flexion crease. It involves a suture suspension (stabilizer) arthroplasty technique, whereby a deep, intra-articular 0 braided polyblended non-absorbable suture is utilized to form a suture suspension sling by anchoring the suture to fixed points of attachments to the flexor carpi radialis insertion and deep ulnar capsule at the base of the index metacarpal, crossing the arthroplasty space and anchoring the radial attachment to the fixed point of insertion of the abductor pollicis longus and dorsal capsule at the dorsal base of the thumb metacarpal. This suture stabilization construct is twice woven back and forth within the arthroplasty space, tightened and firmly sutured over the insertion point of the abductor pollicis longus and dorsal capsule, as longitudinal distraction force and downward (ulnarly-directed) pressure is applied to the metacarpal base. Wrist immobilization is required for only 12-14 days postoperatively, followed by short opponens splinting and active motion, followed by subsequent range of motion and strengthening protocol, with resumption of full use by 3 months postoperatively for the majority of patients. This construct has been shown to effectively stabilize the metacarpal base by tethering it to the index metacarpal via firm anchorage of a heavy non-absorbable suture sling that supports the reconstruction and has been shown to have excellent short-term and long-term, up to 3.5 years, results in the majority of patients, achieving the goals of excellent pain relief, and accurately rebalances the thumb metacarpal with minimal proximal migration (subsidence), excellent restoration of the first webspace angle, and excellent functional recovery with regard to strength and return to activities of daily living. This technique eliminates the specific complications and increased morbidity of the tendon harvesting and transfer procedures and those procedures that require temporary pin fixation or drill holes for tendon passage. This technique does require excessive surgical skill, as it is technically demanding as it requires the skill of back-handed suture passing within a small arthroplasty space. It also requires excision of the entire trapezium to create the suture sling construct and relies on good quality soft tissue for anchorage of the sling.

U.S. Pat. No. 3,496,940 discloses a combined suture and sling for closing an open wound or surgical incision, wherein an elongated strip of flexible hypo-reactive material is formed with a series of integral flexible filaments extending from each longitudinal side edge thereof. The filaments are sewn through the flesh on opposite sides of the wound opening and opposed pairs of filaments are drawn together across the opening and secured to each other to close the wound tightly, with the elongated strip underlying the wound opening and acting as a supporting sling on the under surface of the wound.

U.S. Pat. No. 3,545,008 discloses a tendon prosthesis for use in tendon surgery particularly where there is complete or extensive loss of the tendon, structurally including an elongated member made from a flexible, chemically inert material having at least one flap at each end adapted to overlap the tendon and means for firmly anchoring the prosthesis to the tendon providing a strong, functional anastamotic union.

U.S. Pat. No. 3,805,300 discloses a tendon prosthesis for repair or replacement of a damaged or diseased natural tendon which comprises an elongated member made of biocompatible material having a central portion and two end sections at least one of which has a plurality of longitudinally arranged fenestrations for interweaving with a resected tendon to provide a strong, functional anastomosis. In one embodiment, the second end section of the prosthesis is formed of a pair of flexible cord-like members adapted to anchor the prosthesis to bone structure. In a second embodiment, both end sections include fenestrations allowing each end section to be secured to interwoven segments of a resected tendon.

U.S. Pat. No. 4,187,558 discloses a surgically implantable skeletal ligament having secured thereto at least one deformable collar having a velour-like outer surface adapted to invite tissue ingrowth. In use, the collar portion of the ligament is positioned within a surgically prepared passageway in a bone to protect the ligament from bone abrasion and to assist in ligament attachment by accepting tissue ingrowth into the velour-like surface.

U.S. Pat. No. 4,713,075 discloses a prosthetic device for repairing or replacing connective tissue such as ligaments and tendons in the human or animal body is described. The device comprises a cord of artificial connective tissue formed from a composite, partly absorbable thread. The thread comprises a combination of permanent material and absorbable material susceptible to being dissolved into surrounding living tissue. The dissolving of the absorbable material leaves space for the living tissue to grow into and adhere to the structure formed by the permanent material.

U.S. Pat. No. 4,775,380 discloses a prosthetic ligament for implantation between at least two bones and which takes the form of a tubular body made of woven flexible material through which tissue ingrowth can take place after implantation. A cord is attached to one end of the ligament to thread and to pull the ligament through channels formed in the bones, and a protective detachable sheath is attached to the ligament in order to facilitate the implantation of the ligament as it is pulled through the channels, the sheath immediately thereafter being detached. A bone plug introducer is used to insert a bone plug into one end of the ligament within the bone tunnel, which thereby secures the ligament end in position.

U.S. Pat. No. 6,010,447 discloses a sling device for implant in a human body as a bladder support includes a rectangular, flexible strip of cloth with stiffening members extending across each of the two shorter sides. The stiffening members at each end include a pair of spaced, parallel beams, integrally connected at their ends. Marginal end portions of the flexible strip are passed through the space between the beam around one of the beams, and folded back upon and affixed to the opposing surface of the flexible strip. A flexible suture is attached to a loop at the midpoint of the other beam.

U.S. Pat. No. 6,042,534 relates to prefabricated urethral suspension slings, methods of making the slings, methods of attaching suture to the slings, kits comprising the slings, and methods of using the slings to treat urinary incontinence. The slings comprise a biocompatible material having an elongate shape adapted for urethral suspension. The material has a central portion extending longitudinally between a first end portion and a second end portion. Each end portion of the sling contains at least one suture receiving site. The suture receiving sites are formed prior to surgery and may be reinforced through a variety of means. Sutures may be attached to the suture receiving sites during the manufacturing process or by the physician prior to or during surgery. Additionally, the end portions of the sling containing the suture receiving sites may be thicker than the central portion of the sling.

U.S. Pat. No. 6,110,101 discloses a sling for supporting the urethra and neck of the bladder to prevent urinary incontinence is disclosed. The sling is designed to provide sufficient support to inhibit the unintended flow of urine, yet stretch in a controlled fashion so that the bladder can be voided at approximate times.

U.S. Pat. No. 6,517,578 describes a graft suspension device for suspending a ligament in a bone hole. The suspension device comprises a first loop and second loop suspended from an anchor and has a cradle at the opposite end of the loop to the anchor. Ligament grafts are looped over the cradle and loose ends may be pulled by finger loops whereby the surgeon can adjust the distance of the cradle from the anchor thereby tensioning the grafts as desired.

U.S. Pat. No. 6,872,227 discloses a strip-like implant that has a tape with a first end and with a second end. In the area of at least one of the two ends, a disk-like application aid aligned with the plane of the tape is arranged. The disk-like application aid can also be constructed in the shape of two jaws of a surgical gripping instrument which is set up to grip an implant tape.

U.S. Pat. No. 7,083,568 discloses an implantable article and method of use are disclosed to treat urological disorders. The biocompatible device includes a sling assembly configured to be minimally invasive and provide sufficient support to the target site. In addition, the configuration of the sling assembly also allows the position of the sling to be permanently changed during and/or after implantation.

U.S. Publication No. 2002/0019670 discloses an implantable tissue augmentation device having a multiplicity of biocompatible strands, each of said strands having at least one end wherein the multiplicity of strands are integrally joined at the at least one end of each of the multiplicity of strands. Optionally, the augmentation device has an attachment feature allowing easy attachment to a suture, a needle or other surgical instrument. The strands can have various cross sectional configurations such as rectangles or polygons.

U.S. Publication No. 2002/0123750 relates to orthopedic implants made from a mesh material. The mesh material can be treated in order to promote bone growth, to provide antibiotics, or to provide other beneficial treatment. Specific applications for the implants include, for example, a prosthetic ligament, a tension band, an interbody device, or a fixation device that extends across one or more joints or fractures.

U.S. Publication No. 2006/0149261 discloses a spacer member that is intended to be placed between the ends of the bones which are to be connected, one end of the spacer member being designed to form a joint surface against one of the bone ends. A joint-stabilizing connection is arranged to connect the bones. The spacer member is made of at least one tissue-compatible material.

U.S. Publication No. 2006/0241617 discloses a bone plate and method of forming a bone plate having a plurality of suture loops pre-attached to the bone plate. The suture loops may be flexible and formed of a strong suture material. The suture loops may have various shapes, forms and configurations and may be provided on the bone plate in any number, depending on the characteristics of the fractured bone or bone segments, or of the plate design. Preferably, the suture loops are attached to a surface of the bone plate. The suture loops may receive a strand of suture for fixation of soft tissue to the bone plate.

U.S. Publication No. 2009/0018655 discloses a biocompatible implants that combine a scaffold material for supporting long term repair of a soft tissue with an elongated member such as a suture for aiding in placement of the scaffold during a surgical procedure as well as for immediate mechanical reinforcement of a repair site. The components of an implant are combined such that a longitudinal load placed upon a composite structure can be borne primarily by the elongated member and the scaffold material is isolated from the longitudinal load. Thus, the scaffold material of a composite can be protected from damage due to applied loads and stresses during and following a surgical procedure.

PCT Publication No. WO 2006/034719 discloses a stent which is composed of an external rigid skeleton shaped like an incurving rectangle made of the organically inert substance (Polypropylene). The area in the center on the inside area of the skeleton is filled with a macroporous polypropylene mesh (pores>78 um). Fixed to each of the four corners of the stent is a surgical thread (3) made of Polydioxanone (PDS) number Zero (1-0) with a swaged on curved needle. The stent is of two different sizes to accommodate variations in vaginal capacity. The large measures: 9 cm in length, 5 cm in width and 5 mm in thickness. The small measures: 7 cm in length, 3.5 cm in width and 3.5 mm in thickness.

PCT Publication No. WO 2007/002071 discloses surgical procedures, kits and implants for alleviating human incontinence, and particularly providing improved methods and apparatus to secure a urethral sling to pubic bone to support the urethra and alleviate incontinence are disclosed. Bone anchors are driven into pubic bones with elongated bone anchor sutures configured to be passed through openings of a urethral sling. Suture retainers are applied to the sutures to apply retentive force to the urethral sling to maintain the fixation of the urethral sling proximate to the pubic bone.

Existing surgical devices and methodology, as described above, exhibit several unique drawbacks and disadvantages. In the case of artificial joint replacement surgery, several complications may be encountered; including fracture, bosening, subluxation or dislocation, particulate synovitis and other reported complications that may result in eventual failure of the implant. Additionally, surgical implants designed for other parts of the human body have been difficult to adapt to basal joint arthroplasty, due to the complex nature of the anatomy of the basal joint, the arthritic deformity of subluxation and adduction contracture that occurs with progression of basal joint arthritis, and the cantilever forces applied across the metacarpal base. More complex soft tissue reconstructive methods for basal joint arthroplasty can be associated with the potential for greater short and occasionally long-term impairment of the hand, requiring prolonged rehabilitation. Many of these methods involve more extensive (and at times multiple) surgical incisions, sacrificing normal tendons that are utilized to stabilize the basal joint after trapeziectomy and must be re-directed via bone drill holes to support the thumb metacarpal base. The abductor pollicis longus suspensionplasty technique as disclosed in the American Society for Surgery of the Hand Correspondence Newsletter, DelSignore, 2004-52, August, 2004 eliminates the need to re-direct a tendon through a drill hole, but does sacrifice a slip of the abductor pollicis longus tendon and utilizes an incision which crosses proximal to the wrist flexion crease, requiring immobilization for 4 weeks and thus can be associated with increased morbidity of wrist stiffness and longer recovery, as seen with the other soft tissue tendon-sacrificing techniques. In order to successfully reconstruct an advanced stage arthritic basal joint, all arthritic surfaces must be addressed. The important volar oblique ligament function must be restored, the base of the thumb metacarpal must be approximated close to the base of the index metacarpal, thereby regaining and improving first webspace abduction angle, and the joint arthroplasty space should be preserved to prevent proximal migration and subsequent weakness and collapse deformity. With the utilization of the basal joint stabilizer sling, these goals can be accomplished, with less morbidity, smaller incision, shorter operative time, less demanding surgical technique, and faster short term recovery with earlier resumption of activities of daily living.

SUMMARY OF THE INVENTION

Accordingly, one object of the techniques and apparatus discussed herein is to create an intra-articular basal joint stabilizer sling to serve as a reconstructive implant to treat basal joint arthritis. This basal joint stabilizer sling, made of either synthetic material (mesh, tape, bioabsorbable, biocompatible, or woven fabric), or biologic material (xenograft, autograft, allograft, or human tissue from regenerative tissue matrix), interwoven with strong non-absorbable suture, is firmly anchored via suture anchor to a fixed point of insertion into the radial base of the index metacarpal near the flexor carpi radialis insertion ulnarly, and the volar-radial articular base of the thumb metacarpal radially, via two small holes, created with a small drill into the volar-radial articular surface of the thumb metacarpal through which the suture can be passed on swaged-on curved, slightly curved or straight needles, creating a direct bone-to-bone attachment for the stabilizer sling. Alternatively, the stabilizer sling could be attached radially to the base of the thumb metacarpal with a second suture anchor, or the sling could be secured with soft tissue-to-soft tissue attachments by attaching the sling to the flexor carpi radialis at its insertion onto the base of the index metacarpal and deep ulnar capsule ulnarly and the abductor pollicis longus and dorsal capsule radially. A third alternative would be to attach the sling via suture anchor into the base of the index metacarpal ulnarly and to the soft tissue of the basal joint capsule radially, along a direct line of pull from the base of the index metacarpal.

This technique and implant design provides a simpler, less invasive method for basal joint reconstruction with less donor site morbidity, earlier institution of motion postoperatively, faster healing time and resumption of normal activities, and none of the complications which are uniquely associated with other techniques such as improper drill hole placement or fracture associated with the creation of bone tunnels necessary for passing tendon grafts, malalignment of metal or synthetic implant device into bone, implant breakage, pin tract complications, including infection, hypersensitivity or chronic pain from neuroma formation, as well as the potential loss of function including stiffness of the wrist and hand, which may result from more extensive surgery and lengthy immobilization required in procedures which involve sacrificing and utilizing tendons for stabilizing the reconstruction. The technique of this concept appropriately addresses the larger patient population who suffer from advanced, pan-trapezial, basal joint arthritis by removing the entire trapezium and stabilizes the thumb by tethering it to the base of the index metacarpal, maintaining first web space abduction alignment and preserves the resection arthroplasty space by minimizing proximal migration. This method could also be appropriate for patients with earlier stage trapeziometacarpal arthritis, as the stabilizer sling insertion method and anchorage with a suture anchor into the radial base of the index metacarpal and passage of the suture through two small holes created in the volar-radial articular base of the thumb metacarpal via curved, slightly curved or straight swaged-on needles, or with a second anchor into the base of the thumb metacarpal articular surface, can be accomplished through a small incision, suitable even if the surgeon chooses a hemi-trapeziectomy (partial distal resection) procedure.

One aspect of this disclosure is directed to the fact that utilization of an intra-articular basal joint stabilizer sling, interwoven with strong non-absorbable or long-lasting absorbable suture, firmly anchored to fixed points of bony insertion at radial base of the index metacarpal ulnarly, and the volar-radial articular base of the thumb metacarpal radially avoids the need for sacrificing a functioning tendon, in part or in whole.

Another aspect of this disclosure is the distinct advantage of performing basal joint reconstruction which firmly tethers the base of the thumb metacarpal in close approximation to the base of the index metacarpal, thereby balancing the thumb in an abducted and distally tethered position, thereby restoring the function of the incompetent volar oblique ligament, maintaining joint arthroplasty space and preventing proximal migration.

Yet another aspect of this disclosure provides the ability to perform basal pint arthroplasty through a smaller incision which does not cross the wrist flexion crease, without the need for sacrificing and re-directing tendons through bone tunnels. This method avoids the need for stabilization with pins and thus avoids the well-known complications and morbidities associated with pin fixation.

Still another aspect of this disclosure provides the fact that, since no tendons are harvested and the incision remains distal to the wrist flexion crease, early active range of motion can commence at 12-14 days post-operatively, which will be associated with an earlier return of wrist motion, less stiffness, and more rapid recovery in the early healing phases of rehabilitation.

Yet another aspect of this disclosure provides the fact that the implantation of a basal joint stabilizer sling can be more easily performed by hand surgeons, with greater reliability of outcomes, due to the simplicity of the design, firm bony anchorage into fixed points of insertion, ease of performance and anticipated uniform results, as the technique is not as technically demanding as many of the previously described soft tissue techniques. This technique, when applied with the preferred embodiment design, does not require the precise formation of bone tunnels for tendon passage or need for tendon sacrifice and transfer. There is far less risk of technical failure when compared to artificial metallic, synthetic, or silicone joint implants due to improper bone cuts and potential malalignment of components, since artificial joint replacement procedures do require a steep learning curve, are more costly, and have several pitfalls associated with improper implantation technique when inserting metallic or artificial prostheses into osteoporotic bone that can lead to implant failure, loosening, malalignment, fracture, and subluxation. Even with meticulous technique, artificial joint implants have had a high failure rate.

Further objects, features, and advantages of the techniques and apparatus disclosed herein will be apparent to those skilled in the art from detailed consideration of the preferred embodiments that follow.

BRIEF DESCRIPTION OF THE DRAWINGS

For all figures, the perspective view is from the dorsal side (back) of the right hand such that the thumb is to the left, referred to as the radial side or edge, and the index finger and other fingers are to the right, referred to as the ulnar side or edge. The basal joint stabilizer sling and alternative embodiments disclosed herein exhibit rotational symmetry and hence can be implanted in either the right or left hand.

FIG. 6A is a diagram of an alternative embodiment of the stabilizer sling. The sling configuration is similar to the configuration of FIG. 1 except the central portion 102 of the sling is oval and the suture 101 is woven through the central portion 102 of the sling closer to the periphery of the sling. The ulnar side 104 of the sling has a suture anchor 106 embedded into the ulnar edge of the sling and the two ends of the suture 101 emerging from the radial side 105 have swaged-on curved, slightly curved or straight needles 100 attached.

FIG. 6B is a diagram of the implantation of the sling of FIG. 6A. The basal joint stabilizer sling center section 102 has been anchored in place on the ulnar edge 104 using a suture anchor 106, which is embedded into the ulnar edge of the sling, and inserted into the radial base of the index metacarpal 307. On the radial edge, the exiting sutures are utilized to attach the radial edge 105 of the sling to soft tissue, including joint capsule, (not shown) in a direct line of pull from the base of the index metacarpal. The two sutures 101 are tied off with multiple square knots 303. The flexor carpi radialis 302 and abductor pollicis longus 304 tendons are identified in the figure.

DETAILED DESCRIPTION OF PREFERRED EMBODIMENTS

Figure 1A:
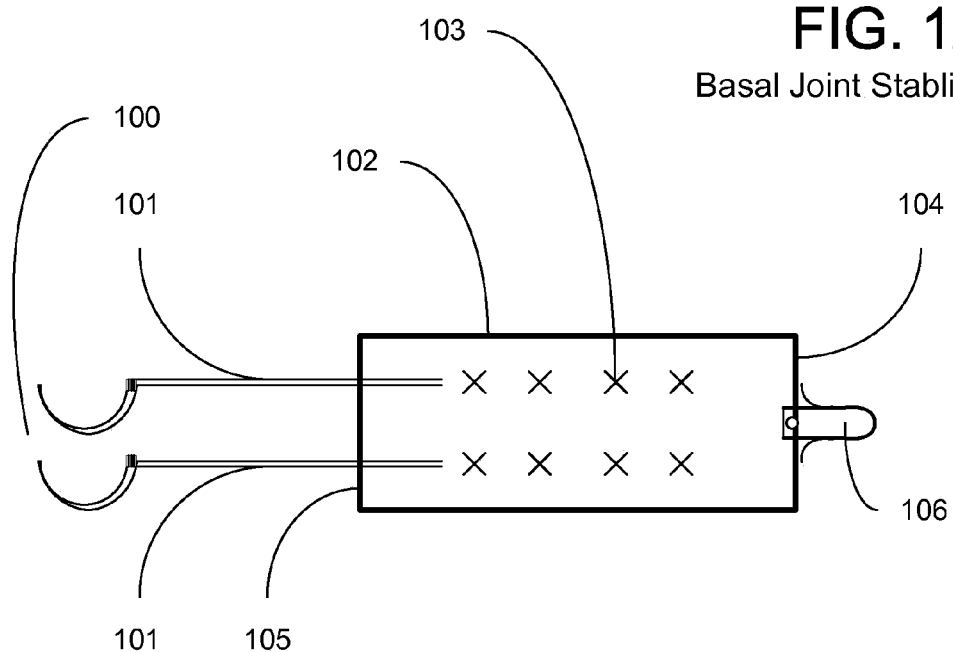
FIG. 1A is a schematic representation of the basal joint stabilizer sling, showing a rectangular central section 102. This preferred sling embodiment is configured such that a single suture with two sutures ends, 101 having attached swaged-on curved, slightly curved or straight needles 100 enters the radial edge 105, traverses the sling body 102 with a plurality of interlaced cross-stitches 103, passing through the central portion of the sling, enters a hole near the bottom of a suture anchor 106 embedded into the ulnar edge 104, re-traverses the sling body 102 with a plurality of interlaced cross-stitches 103, and emerges from the radial edge 105.

The techniques and apparatus disclosed herein enables surgeons to treat basal joint arthritis with a reconstructive method that allows for simplicity, ease of performance, more predictable outcome among surgeons of varied backgrounds, training and ability, shorter operative time, lower surgical site morbidity, smaller incision, no need for harvesting and sacrificing of functioning tendons, no pin fixation, faster recovery, and earlier return to activities of daily living.

This technique and implant design will provide a simpler, less invasive method for basal joint reconstruction with less donor site morbidity, earlier institution of motion post-operatively, faster healing time and resumption of normal activities, and none of the complications that are uniquely associated with other techniques.

The benefits of these concepts are enhanced by meeting the goals of basal joint reconstruction which include removal of the entire arthritic interface, particularly important for those patients with the more common form of advanced, pan-trapezial arthritis, along with reconstruction of the function of the important volar oblique ligament, maintenance of the first web space abduction angle by approximating the base of the thumb metacarpal towards the base of the index metacarpal, maintenance of joint arthroplasty space by distally tethering the base of thumb metacarpal towards the base of the index metacarpal, and correction of the arthritic subluxation deformity.

In describing the techniques and apparatus disclosed herein, the following term(s) have been used in the description.

The term "terminally sterilized" refers herein to a device that has been rendered sterile by demonstrating a sterility assurance level (SAL) of at least $10^{-6}$ with *B. stearothermophilus* spores, an organism that has been shown to be highly resistant to any sterilization process. Terminally sterilized also refers to a sterilization procedure which passes the requirements of the Association of Official Analytical Chemists (AOAC) Sporicidal Test and has the ability to sterilize medical devices containing diffusion-restricted areas, including mated surfaces and lumens.

The term "sutures" refers to surgical suture materials made from non-absorbable synthetic substances such as polyester multifilament, braided polymer blends, wire, or nylon monofilament. Sutures are sized by the United States Pharmacopoeia scale from largest 5=0.70 mm in diameter to the smallest, 10-0=0.020 mm in diameter and may consist of a single 0 sized non-absorbable suture, or a double 2-0 size non-absorbable suture or some other combination of threads.

The term "absorbable sutures" refers to surgical suture materials made from substances that gradually dissolve in a matter of weeks and are eventually removed by the body.

The term "long lasting absorbable sutures" refers to surgical suture materials made from substances that dissolve in 18 to 24 months and are eventually removed by the body.

The term "strong material" or "strong suture" includes non-absorbable and long lasting absorbable surgical suture capable of performing tendon repairs having a tensile strength in the range of substantially 15 newtons to 70 newtons depending upon the suture method employed. The concept of a "strong suture" is explored in depth by Shaieb and Singer in the Journal of Hand Surgery (British and European Volume, 1997) 22b: 6: 764-767, which is hereby incorporated by reference.

The term "Wagner incision" refers to a midaxial incision along the volar-radial aspect of the thumb metacarpal base, which extends proximally along the radial border of the thenar eminence, between the glabrous and non-glabrous skin, and extends ulnarly, just distal to the wrist flexion crease.

The term "xenograft" refers to the transplantation of living cells, tissues, or organs from one species to another such as from pigs to humans.

The term "autograft" refers to tissue transplanted from one part of the body to another in the same individual. An autograft is also called an autotransplant.

The term "allograft" refers to tissue transplanted from a human cadaver that is utilized for implantation in a living human.

The term "subluxation" refers to an incomplete or partial dislocation of a joint.

The term "drill hole" refers to holes drilled into bone for the purpose of inserting and holding suture anchors. These drill holes are on the order of 2.0-2.4 mm (0.079-0.094 inch) in diameter and are made to place non self-tapping suture anchors. Self-tapping suture anchors can be inserted into bone without the need for making drill holes.

The term "small drill hole" refers to holes in bone, created with a small drill bit for the purpose of threading, with a swaged-on curved, slightly curved or straight needle, non-absorbable or long-lasting absorbable sutures emerging from the radial edge of the sling through the small drill holes to firmly anchor the radial edge of the sling to the base of the thumb metacarpal. These sutures are tightly tensioned and secured with multiple square knots over the dorsum of the thumb metacarpal over a bone bridge. These drill holes are made with a wire or a small drill bit on the order of 1.14-1.37 mm (0.045-0.054 inch) in diameter.

The term "suture anchor" refers to the class of generic non-metallic and metallic devices placed into bone to enable the attachment of soft tissue to bone. Various configurations of suture anchors are discussed by Philippe Saffar, Peter C. Amadio, and Guy Foucher in Current Practice in Hand Surgery, Informa Healthcare, 1997, which is hereby incorporated by reference.

The term "apparatus" refers to any of the several variations of the basal joint stabilizer sling, sutures, swaged-on curved, slightly curved or straight needles, suture anchors and combinations there of.

The term "embedded" refers to attachment of a suture anchor to the central portion of the stabilizer sling along an edge where the base of the suture anchor abuts or slightly projects into the central portion such that the suture that runs through the hole in the base of the suture anchor maintains approximately continuous contact with the central portion except for the small segment which lies within the central hole of the suture anchor.

For a general understanding of the techniques and apparatus disclosed herein, reference is made to the drawings. In the drawings, like reference numerals have been used to designate identical elements.

Figure 1B:
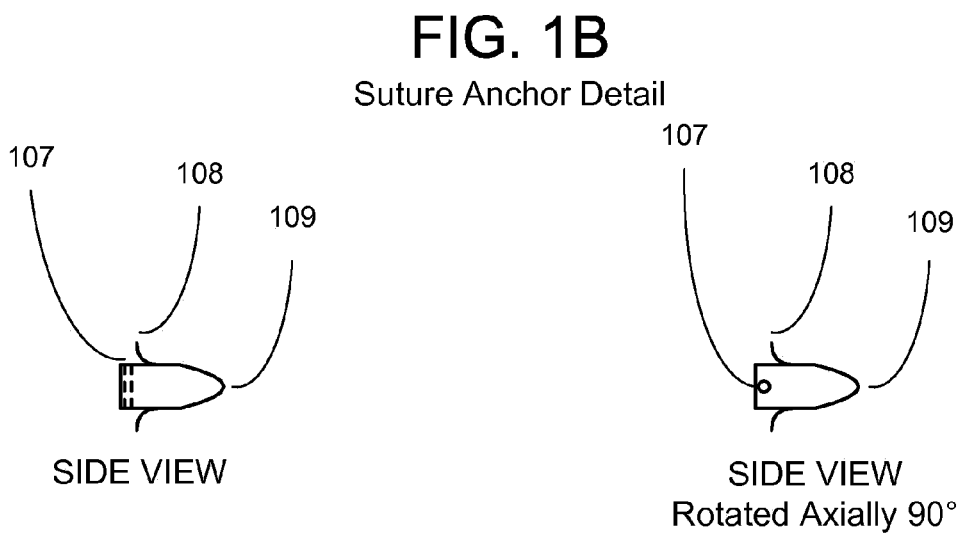
FIG. 1B is two views of the details of the suture anchor. The side view shows the suture anchor body 109 having a plurality of detents 108 to hold the suture anchor in place once inserted in a hole in bone. The base of the suture anchor body 109 has a pre-manufactured circular hole 107, oriented parallel to the drawing, to accept a suture. The side view rotated axially 90° shows the pre-manufactured circular hole 107 in the base of the suture anchor body 109 such that the circular hole's orientation is perpendicular to the drawing.
Figure 2A:
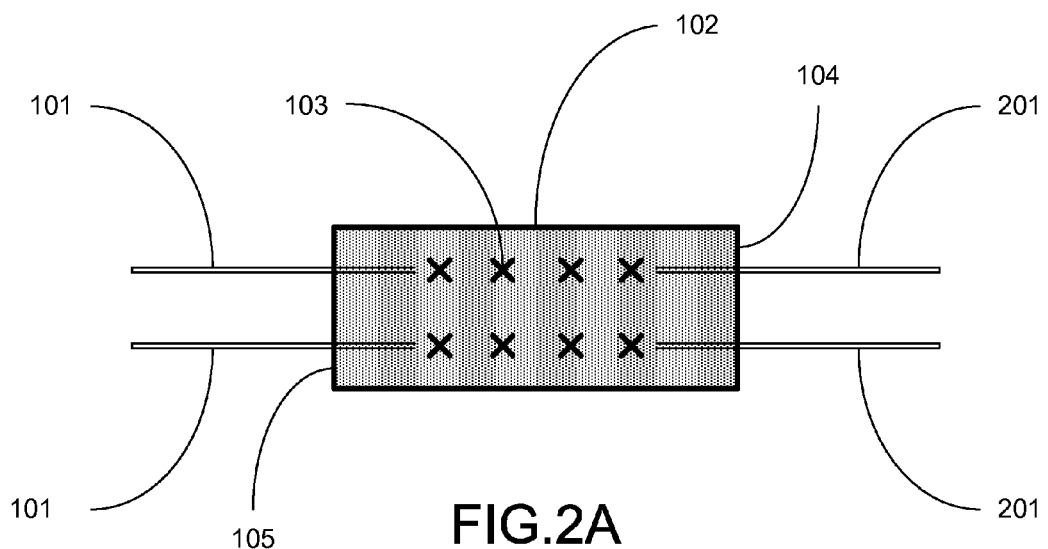
FIG. 2A is a plan diagram of a preferred embodiment of the basal joint stabilizer sling showing a center section 102 where the sutures 101 on the radial edge 105 and sutures 201 on the ulnar edge 104 are attached to the center section 102 by a plurality of interlaced cross-stitches 103. The sutures 101 and 201 are not swaged onto suture anchors or needles in this embodiment. This preferred sling embodiment is configured such that there are two sutures ends 101 emerging from the radial edge 105 and two sutures ends 201 emerging from the ulnar edge 104.
Figure 2B:
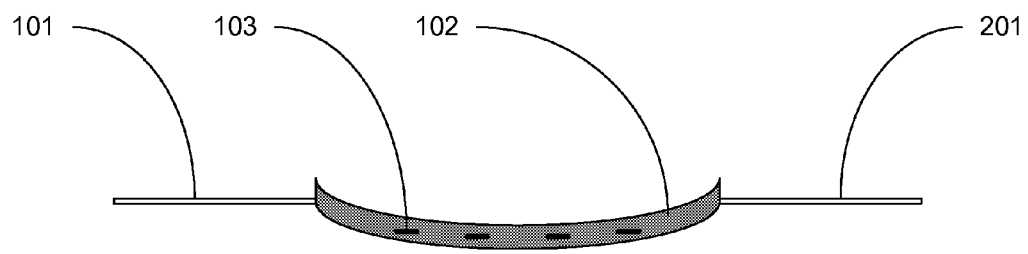
FIG. 2B is a side view of a modified basal joint stabilizer sling. The plurality of interlaced cross-stitches 103 and attached sutures 101 and 201 are indicated.

FIG. 1 is a diagram of the schematic representation of the preferred embodiment of the basal joint stabilizer sling, showing a rectangular central section 102 where a strong, central core non-absorbable single braided suture 101 enters the radial edge 105, is woven through the sling 102, with a plurality of interlaced cross-stitches 103. This suture passes through the hole in a suture anchor 106 embedded into the ulnar edge of the central portion 102 of the sling. The suture 101 then weaves through the central portion of the sling 102 with a plurality of interlaced cross-stitches 103 and exits through the radial edge 105. The radial edge suture ends 101 are attached to swaged-on curved, slightly curved or straight needles 100 which are utilized to attach the radial edge of the sling to the volar-radial articular base of the thumb metacarpal through two small holes.

Figure 3:
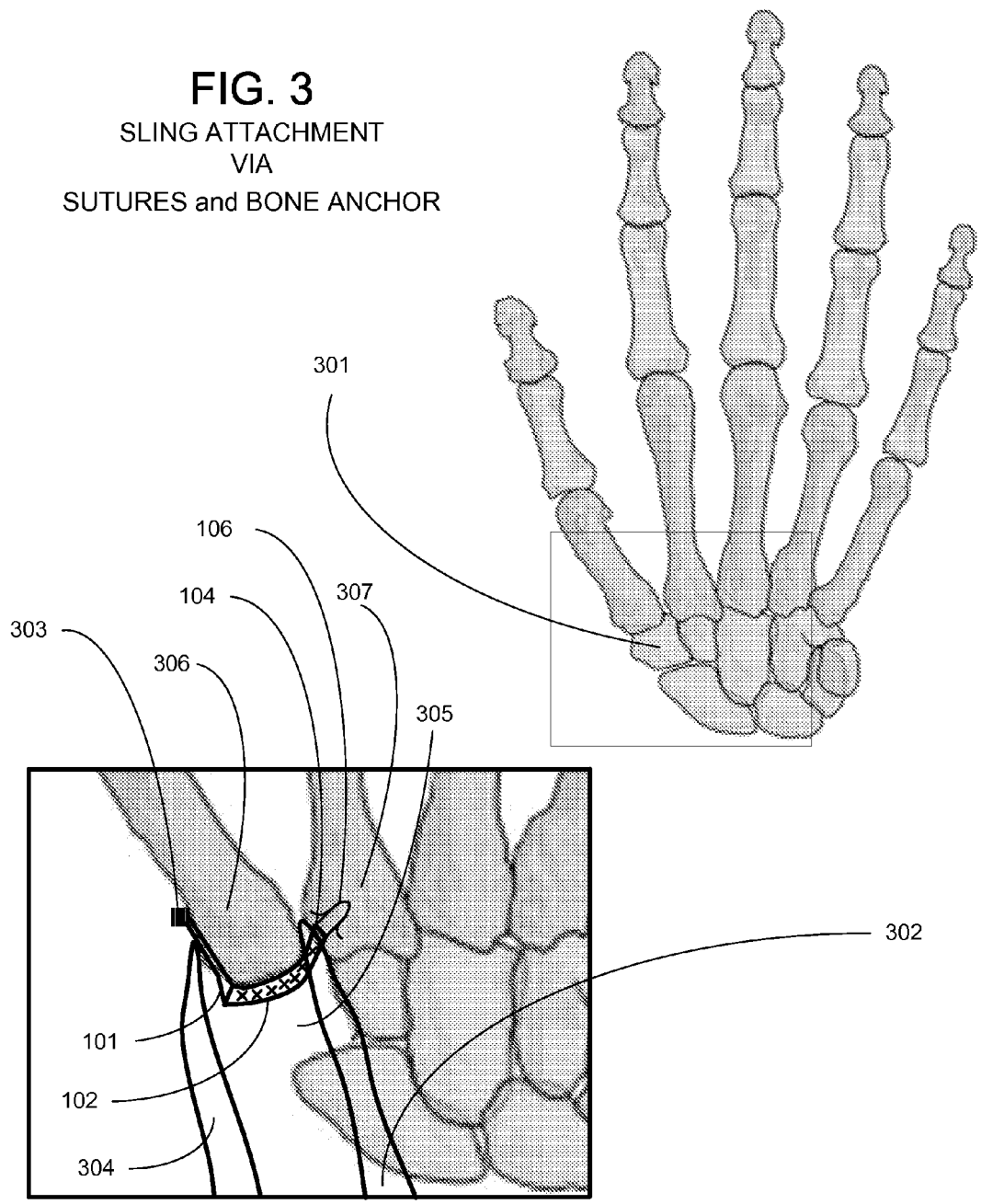
FIG. 3 is a diagram of the bones of the hand where the enlarged section shows that the trapezium 301 has been removed, leaving the arthroplasty space 305, and the basal joint stabilizer sling center section 102 has been anchored in place on the ulnar edge 104 using a suture anchor 106 which is embedded into the ulnar edge of the sling and inserted into the radial base of the index metacarpal 307. The suture anchor 106 is able to resist pull-out forces. On the radial edge, the exiting sutures are utilized to attach the radial edge 105 of the sling to the volar-radial articular base of the thumb metacarpal 306 through two small holes, made with a small drill. The two sutures 101 are tied off with multiple square knots 303. The flexor carpi radialis 302 and abductor pollicis longus 304 tendons are identified in the figure.

The preferred basal joint stabilizer sling embodiment is configured such that there are two sutures ends 101 with attached swaged-on curved, slightly curved or straight needles emerging from the radial edge 105 and a suture anchor 106 embedded into the ulnar edge 104 of the central portion of the sling 102. The suture associated with the central portion of the suture within the stabilizer sling is interwoven throughout sling 102 with interlocking stitches 103. This central portion 102 is composed of terminally sterilized material made of either synthetic material (mesh, tape, bioabsorbable or biocompatible material or woven fabric), or biologic material. Appropriate biodegradable synthetic material includes polyurethane ureas, polylactides, polydiaxones, poly-R-hydrobutylates, and other suitable flexible, but non-elastic polymers. Appropriate non-biodegradable synthetic materials include poly(ethylene terephthalate), polytetrafluoroethylene, silicone, perfluoroalkoxy polymer, fluorinated ethylene propylene polymer, and other suitable flexible, but non-elastic polymers. Appropriate biologic materials include xenograft, allograft, autograft, and/or human tissue from regenerative tissue matrix. Alternatively, the central portion of the sling could be composed of long-lasting absorbable sutures made from substances that dissolve in 18 to 24 months and are eventually removed by the body. This sling and the sutures arising from the sling could be made of the same material as an all-in-one construct with the ends of this sling comprised of sutures, two of which extend out through the radial edge 105 of the sling, to be attached to curved, slightly curved or straight needles in one embodiment, or an second anchor 400 in another method. The suture braided within the sling itself could traverse the ulnar edge 104 of the sling where the suture will pass through the anchor 106 which is embedded into the ulnar edge 104 of the sling. This all-in-one construct of sling material and matching suture will act as a single structure and the sutures which extend beyond the edge of the sling will serve as a substitute for the sutures described in the described embodiments. The flexibility of the synthetic and biologic materials allow the center section 102 of the basal joint stabilizer sling to be deformable and to conform to the base of the thumb metacarpal 306. The synthetic materials are made with surfaces that are either porous or non-porous depending upon the specific application. Porous surfaces potentially allow the ingrowth of new biological tissue firmly holding the implant in place. In FIG. 3, the enlarged section shows that the trapezium 301 has been removed leaving the arthroplasty space 305 and the basal joint stabilizer sling center section 102 has been secured in place on the ulnar side by the suture anchor 106 being inserted into the radial base of the index metacarpal 307. On the radial edge, the exiting sutures 101 are utilized to attach the radial edge 105 of the sling to the volar-radial articular base of the thumb metacarpal 306 through two small drill holes. FIG. 3 shows the closely approximated relationship of the base of the thumb metacarpal 306 towards the base of the index metacarpal 307. Note that the first web space abduction angle has been restored by tethering the base of the thumb metacarpal 306 to the base of the index metacarpal 307. Note also the distal tethering of the thumb, minimizing proximal migration and preserving the joint arthroplasty space 305.

The preferred surgical procedure for basal joint arthroplasty using the preferred embodiment of the basal joint stabilizer sling is as follows:

A Wagner incision is utilized, at the junction of the glabrous and non-glabrous skin, curving ulnarly at the proximal edge of the basal joint remaining distal to the wrist flexion crease. The thenar muscles are stripped off the volar aspect of the basal joint capsule and reflected ulnarly, exposing the capsule in entirety. A longitudinal incision is made in the basal joint capsule, with medial and lateral flaps being sub-periosteally elevated and preserved for later repair. The flexor carpi radialis 302 and abductor pollicis longus 304 tendons are identified and their insertion sites are carefully preserved as the entire trapezium 301 is removed. Following trapeziectomy, longitudinal distraction force is applied to the thumb, pulling it as far distally as possible, exposing the flexor carpi radialis 302 insertion onto the base of the index metacarpal 307. The basal joint stabilizer sling, with the attached suture anchor embedded into and emerging from the ulnar edge 104 is then placed into the joint arthroplasty space 305, and the suture anchor 106, which is attached to a suture loop 101 coincident with and embedded into the ulnar edge 104 of the stabilizer sling, is then firmly inserted into the exposed radial base of the index metacarpal 307, just radial to the flexor carpi radialis insertion, rigidly affixing the ulnar edge 104 of the sling to the index metacarpal base 307. The stabilizer sling is brought across the arthroplasty space 305 with the sutures ends 101 emerging from the radial edge 105 of the basal joint stabilizer sling center section 102 being swaged onto curved, slightly curved or straight tapered surgical needles 100. Two small holes are made in the volar-radial base of the thumb metacarpal articular surface with a small drill, to allow passage of swaged-on curved, slightly curved or straight needles 100 attached to the sutures 101 arising from the radial edge of the sling through these holes. With continual firm longitudinal traction being applied to the thumb, the basal joint stabilizer sling is drawn tightly across the arthroplasty space 305, and the two remaining free ends of the suture 101 emerging from the radial edge 105, are passed by directing the tapered needles 100 from within the arthroplasty space 305, out through the small holes in the base of the thumb metacarpal 306. Tension is applied to the sutures, as downward (ulnarly directed) pressure is placed on the dorsal base of the thumb metacarpal 306, approximating and tethering it towards the base of the index metacarpal 307, while continually maintaining a distal longitudinal distraction force. The radial edge 105 sutures 101 which are passed through the thumb metacarpal small drill holes are secured with multiple square knots 303 over a bony bridge, drawing the basal joint stabilizer sling tightly across the arthroplasty space 305. If desired, additional reinforcement can be achieved by placing a heavy non-absorbable #0 suture as a suture suspension arthroplasty, as disclosed in *Suture Suspension Arthroplasty Technique for Basal Joint Arthritis Reconstruction*, DelSignore and Accardi, to be published in Techniques in Hand and Upper Extremity, December, 2009. This additional suturing method can provide additional support, creating a suture suspension bridge just proximal to the stabilizer sling and serves to augment the first web space abduction angle. The basal joint capsule is repaired with 3-0 polyester multifilament (non-absorbable) suture. The thenar muscles are reattached to the base of thumb metacarpal 306 with 4-0 absorbable suture, completely covering the suture multiple square knots 303 from the basal joint stabilizer sling, and 5-0 nylon sutures are placed in the skin. Post operatively, immobilization in a bulky post-op bandage with a thumb spica plaster splint is worn for 12-14 days, after which bandage and 5-0 nylon sutures are removed and a short opponens orthoplast splint is applied, worn continually for 2 weeks, off only for bathing and gentle active range of motion exercises. Progressive use and strengthening exercises are introduced by 6 weeks post-operative with the splint being discontinued at 8 weeks post-operative. The majority of patients will be released to resume full, unrestricted activities by 12 weeks post-operatively, with some continuing to show improvement with regard to motion and strength for up to 6-12 months post-operatively.

The stabilizer sling with its bone-to-bone attachment will function similar to a "hammock" bridging the arthroplasty space 305 forming a suspension construct to cradle and stabilize the thumb metacarpal 306 with the base of the thumb firmly approximated towards the base of the index metacarpal 307 and tethered distally, supporting the arthroplasty space 305, providing a strong basal joint stabilizer sling, thereby restoring the function of the volar oblique ligament. This construct maintains the first web space abduction angle positioning of the thumb metacarpal 306, maintains the arthroplasty space 305, prevents proximal migration, and approximates and effectively tethers the base of the thumb to the base of the index metacarpal 307.

Figure 4A:
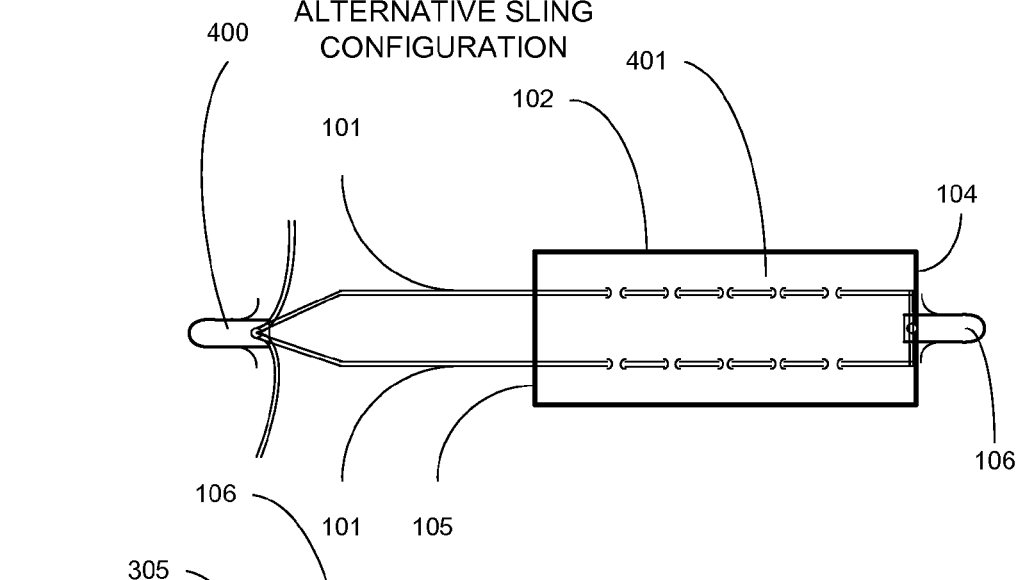
FIG. 4A is a diagram of an alternative embodiment of the basal joint stabilizer sling where both bony attachments are performed with suture anchors on the radial and ulnar sides. This embodiment has a central portion 102 which is rectangular and incorporates a suture 101 which is attached by a simple stitch 401 to the central portion 102 of the sling. On the ulnar side 104, the suture 101 passes through a hole in the base of the suture anchor 106. On the radial side 105, the suture exits the side in two places and is threaded through a hole in the base of a second suture anchor 400.
Figure 4B:
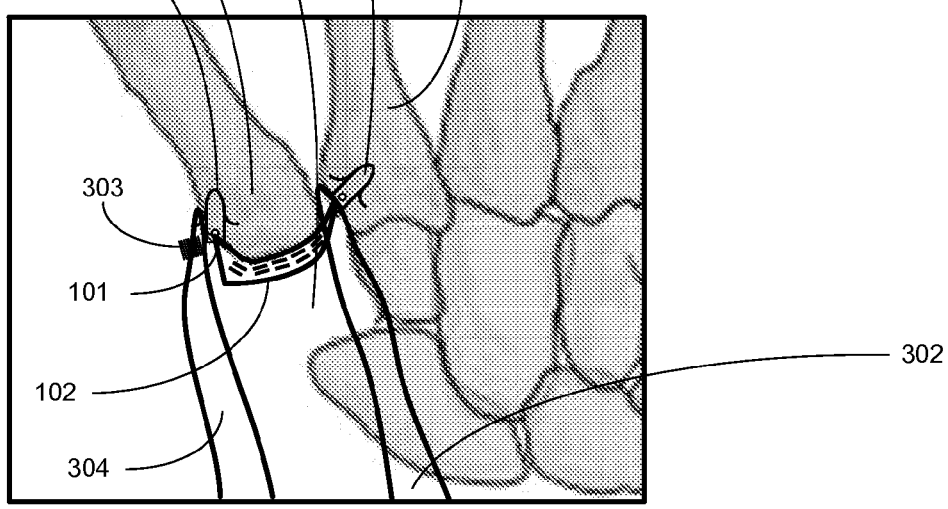
FIG. 4B is a diagram of the implanted stabilizer sling having a central; portion 102. On the ulnar edge 104, a suture anchor 106, which is embedded into the ulnar edge of the sling, is inserted into the radial base of the index metacarpal 307. The second anchor 400 is inserted into the volar-radial articular surface of thumb metacarpal base 306 and is progressively tensioned and secured with a knotless suture technique or with manual tension applied and securing the suture 101 with multiple square knots 303. The flexor carpi radialis 302 and abductor pollicis longus 304 tendons plus the arthroplasty space 305 are identified in the figure.

Another surgical attachment option for the basal joint stabilizer sling involves the implantation of another alternative embodiment of the basal joint stabilizer sling as shown in FIG. 4A where a suture anchor 106 embedded in the ulnar edge 104 of the basal joint stabilizer sling center section 102 is inserted into the base of the index metacarpal 307, and where suture ends 101 emerging from the radial edge 105 of the basal joint stabilizer sling center section 102 are attached to the volar radial base of the thumb metacarpal 306 articular base with a second suture anchor 400. This technique utilizes a Wagner incision, stopping distal to the wrist flexion crease. The thenar muscles are reflected off the underlying basal joint capsule and a longitudinal incision in the capsule is made. The trapezium 301 is removed in entirety and longitudinal distraction force is applied to the thumb. The flexor carpi radialis 302 is traced distally to it's insertion onto the base of the index metacarpal 307. The stabilizer sling is placed into the arthroplasty space 305. The suture anchor 106 embedded in the ulnar edge 104 of the stabilizer sling, is then firmly inserted into the radial base of the index metacarpal 307, rigidly affixing the ulnar edge of the sling to the index metacarpal base. The ulnar edge 104 of the stabilizer sling is thus closely approximated to the index metacarpal 307 base. The second suture anchor 400, through which the suture ends 101 emerging from the radial edge 105 have been previously attached from the manufacturer, is inserted into the volar-radial base of the thumb metacarpal 306 articular surface. Tension is applied to the two suture ends emerging from the radial edge 105 of the sling which pass through the second suture anchor 400, as downward (ulnarly directed) pressure is placed on the dorsal base of the thumb metacarpal 306, approximating it towards the base of the index metacarpal 307, while continually maintaining a distal longitudinal distraction force. With continual firm longitudinal traction being applied to the thumb, the basal joint stabilizer sling is tensioned across the arthroplasty space 305, and the two remaining free ends of the suture 101 emerging from the suture anchor at the radial edge 105 of the stabilizer sling, are tightly secured, fastened and cut off, tethering the base of the thumb metacarpal towards the base of the index metacarpal. If desired, additional reinforcement can be achieved by placing a heavy non-absorbable #0 suture as a suture suspension arthroplasty, as disclosed in article *Suture Suspension Arthroplasty Technique for Basal Joint Arthritis Reconstruction*, DelSignore and Accardi, to be published in Techniques in Hand and Upper Extremity Surgery, December, 2009. This additional suturing method can provide additional support, creating a suture suspension bridge just proximal to the stabilizer sling and serves to augment the first web space abduction angle. The basal joint capsule is repaired with 3-0 polyester multifilament (non-absorbable) suture. The thenar muscles are reattached to the base of thumb metacarpal 306 with 4-0 absorbable suture, and 5-0 nylon non-absorbable sutures are placed in the skin. Postoperative treatment and follow up is the same as described in the case of the preferred operative embodiment. This procedure also maintains the first web space abduction angle positioning of the thumb metacarpal 306, maintains the arthroplasty space 305, prevents proximal migration, and approximates and effectively tethers the base of the thumb metacarpal 306 to the base of the index metacarpal 307. This form of bone-to bone attachment draws the basal joint stabilizer sling tightly across the arthroplasty space 305, similar to a "hammock" bridging the arthroplasty space 305 and forms a suspension construct to cradle and stabilize the thumb metacarpal 306 with the base of the thumb firmly approximated towards the base of the index metacarpal 307 and tethered distally, supporting the arthroplasty space 305, providing a strong basal joint stabilizer sling, thereby restoring the function of the volar oblique ligament.

Figure 5A:
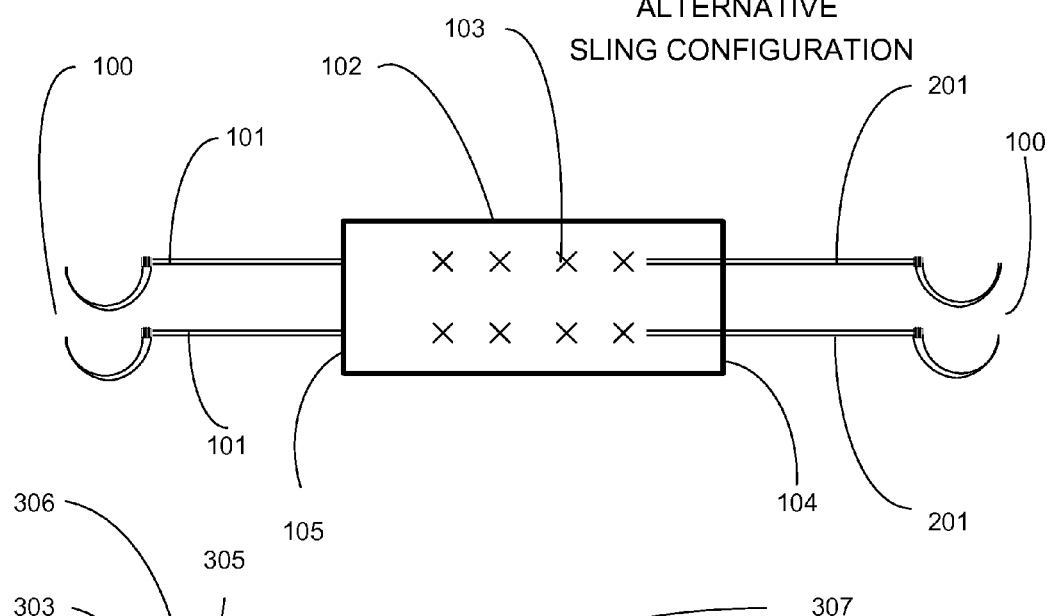
FIG. 5A is a diagram of an alternative embodiment of the basal joint stabilizer sling. Each suture end 101 or 201 is swaged onto a tapered surgical needle 100 for subsequent attachment to tendon insertion and capsule anchoring points. This alternative embodiment is configured such that there are two sutures 101 with attached tapered surgical needles 100 emerging from the radial edge 105 and two sutures 201 with attached tapered surgical needles 100 emerging from the ulnar edge 104. A plurality of interlaced cross-stitches 103 is used to attach the sutures to the central portion 102 of the stabilizer sling.
Figure 5B:
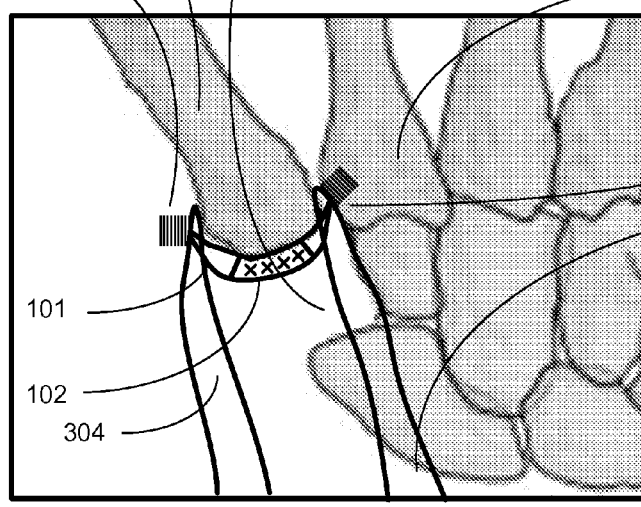
FIG. 5B is a diagram of the implanted stabilizer sling. The sutures 201 arising from the ulnar edge are firmly attached by passing each needle through the flexor carpi radialis 302 at its insertion near the index metacarpal 307, firmly anchoring the ulnar border 104 of the sling with multiple square knots 303 tied deeply within the arthroplasty space 305. The sutures emerging from the radial edge 105 are passed from the arthroplasty space 305, out through the abductor pollicis longus 304 and dorsal capsule as they insert onto the radial base of the thumb metacarpal 306. The sling is tightly tensioned and secured with multiple square knots 303, tethering the base of the thumb 306 towards the base of the index metacarpal 307 with a soft tissue-to-soft tissue construct attachment for the stabilizer sling.

Alternatively, another surgical attachment option for the basal joint stabilizer sling involves the implantation of another alternative embodiment of the basal joint stabilizer sling as shown in FIG. 5A whereas the sling is attached with swaged-on curved needles with soft tissue-to-soft tissue attachments with no bony fixation. The alternative embodiment is configured such that there are two sutures 101 with attached tapered surgical needles 100 emerging from the radial edge 105 and two sutures 201 with attached tapered surgical needles 100 emerging from the ulnar edge 104. As shown in FIG. 5B, this technique utilizes a Wagner incision, stopping distal to the wrist flexion crease. The thenar muscles are reflected off the underlying basal joint capsule and a longitudinal incision in the capsule is made. The trapezium 301 is removed in entirety and longitudinal distraction force is applied to the thumb. The flexor carpi radialis 302 is traced distally to its insertion onto the base of the index metacarpal 307. Following trapeziectomy, longitudinal distraction force is applied to the thumb, pulling it as far distally as possible, exposing the flexor carpi radialis 302 insertion onto the base of the index metacarpal 307. The basal joint stabilizer sling is then placed into the joint arthroplasty space 305, and both needles, swaged onto the sutures 201, emerging from the ulnar edge 104 of the basal joint stabilizer sling, are passed, in opposite directions, through the fixed insertion point of the flexor carpi radialis 302, with additional anchorage by grasping some of the deep ulnar basal joint capsule and flexor carpi radialis 302 sub-sheath. The ulnar edge 104 sutures 201 are tightly tensioned and secured deep within the arthroplasty space with multiple square knots 303, tightly drawing the ulnar edge of the stabilizer sling flush against the flexor carpi radialis 302 insertion near the base of the index metacarpal 307. With continual firm longitudinal traction being applied to the thumb, the basal joint stabilizer sling is brought across the arthroplasty space 305, and the two remaining free ends of the suture 101 emerging from the radial edge 105, are passed by directing the tapered needles 100 from within the arthroplasty space 305, out dorsally, through the fixed insertion point of the abductor pollicis longus 304 tendon and the dorsal basal joint capsule, as they insert onto the dorsal base of the thumb metacarpal 306. Tension is applied to the sutures, as downward (ulnarly directed) pressure is placed on the dorsal base of the thumb metacarpal 306, approximating it towards the base of the index metacarpal 307, while continually maintaining a distal longitudinal distraction force. The sutures 101 are passed twice through the abductor pollicis longus 304 insertion point and are tightly tensioned and secured with multiple square knots 303, drawing the basal joint stabilizer sling tightly across the arthroplasty space 305, similar to a "hammock" bridging the arthroplasty space 305 and forming a suspension construct to cradle and stabilize the thumb metacarpal 306 with the base of the thumb firmly approximated towards the base of the index metacarpal 307 and tethered distally, supporting the arthroplasty space 305, providing a soft tissue attachment for the basal joint stabilizer sling, thereby restoring the function of the volar oblique ligament. This procedure maintains the first web space abduction angle positioning of the thumb metacarpal 306, maintains the arthroplasty space 305, prevents proximal migration, and approximates and effectively tethers the base of the thumb metacarpal 306 to the base of the index metacarpal 307. The sling is tightly tensioned and secured with multiple square knots 303, tethering the base of the thumb towards the base of the index metacarpal with a soft tissue-to-soft tissue construct attachment for the stabilizer sling. If desired, additional reinforcement can be achieved by placing a heavy non-absorbable #0 suture as a suture suspension arthroplasty, as disclosed in *Suture Suspension Arthroplasty Technique for Basal Joint Arthritis Reconstruction*, DelSignore and Accardi, to be published in Techniques in Hand and Upper Extremity Surgery, December, 2009. This additional suturing method can provide additional support, creating a suture suspension bridge just proximal to the stabilizer sling and serves to augment the first web space abduction angle. The basal joint capsule is repaired with 3-0 polyester multifilament (non-absorbable) suture. The thenar muscles are reattached to the base of thumb metacarpal 306 with 4-0 absorbable suture, completely covering the suture multiple square knots 303 from the basal joint stabilizer sling, and 5-0 nylon non-absorbable sutures are placed in the skin. Postoperative treatment and follow up is the same as described in the case of the preferred operative embodiment.

With this alternative embodiment, the stabilizer sling is attached via soft tissue anchorage points only, with sutures arising from the ulnar edge 104 which are firmly attached by passing each needle through the flexor carpi radialis 302 at its insertion near the index metacarpal 307 and firmly anchoring the ulnar border 104 of the sling with multiple square knots 303 tied deeply within the arthroplasty space 305. The sutures 101 emerging from the radial edge 105 are passed from the arthroplasty space 305 out through the abductor pollicis longus 304 and dorsal capsule as they insert onto the radial base of the thumb metacarpal 306.

Alternatively, another surgical attachment option for the basal joint stabilizer sling involves the implantation of yet another alternative embodiment of the basal joint stabilizer sling as shown in FIG. 6A whereas the stabilizer sling is attached on the ulnar side with a suture anchor and on the radial side using suture secured into soft tissue with no bony fixation. The technique of implantation of the stabilizer sling on the ulnar side is the same as the technique used for the implantation of the preferred embodiment stabilizer sling on the ulnar side as shown in FIG. 1 and FIG. 3. The implantation of this embodiment on the radial side; however, differs from the implantation seen in FIG. 5A and FIG. 5B in that the soft tissue attachment is into the basal joint capsule and soft tissues (not shown) in a direct line of pull from the base of the index metacarpal insertion point.

The preferred basal joint stabilizer sling embodiment in FIG. 1A and the alternative basal joint stabilizer sling embodiment in FIG. 4A, as described, both of which utilize bone-to-bone fixation techniques provide the benefits of ease of performance through a small incision, ability to treat early disease for which partial trapeziectomy is warranted, as well as late stage disease for which entire trapeziectomy is required, and the safety, stability as well as greater reliability of bone-to-bone attachment. Although there are some minor increased morbidities and risks associated with placing suture anchors including increased cost, potential anchor pull-out failure in patients with osteoporotic bone and improper anchor placement, the advantages of a simpler, lower morbidity and easily reproducible procedure outweigh the potential disadvantages. If bone fixation is felt to be inadequate, additional soft tissue reinforcement could be considered to provide additional support to the repair. Fixation to soft tissue alone, as described as the second alternative embodiment, can be more difficult as it requires suturing and tying knots deep within the basal joint arthroplasty space and requires entire trapeziectomy, which is not warranted in patients with early stage arthritis, limited to the trapeziometcarpal joint alone. There is also some potential concern that older patients undergoing basal joint reconstruction may not have good quality soft tissue, on which the soft tissue-to-soft tissue alternative fixation must rely. If patients have poor quality soft tissue attachments (or absence of the flexor carpi radials due to pre-operative attritional rupture), the suspension construct is more likely to fail and allow thumb metacarpal subsidence and loss of correction with time. In these cases, bone-to-bone attachment methods would be preferable.

It will be apparent to those skilled in the art that various modifications and variations can be made to the methods, processes and apparatus disclosed herein. Thus, it is intended that these concepts cover such modifications and variations, provided they come within the scope of the appended claims and their equivalents.

The disclosure of all publications cited above is expressly incorporated herein by reference in their entireties to the same extent as if each were incorporated by reference individually.

What is claimed is:

1. A method for performing basal joint arthroplasty, the method comprising:
providing an implantable sling, the implantable sling comprising:
a central section, a first suture attached to said central section, and a second suture attached to said central section;
a first suture anchor attached to said first suture and configured for disposition in an index metacarpal at a first attachment point; and
a second suture anchor attached to said second suture and configured for disposition in a thumb metacarpal at a second attachment point;
creating an access portal for performing a basal joint arthroplasty;
performing a trapeziectomy to create an arthroplasty space;
positioning said central section in said arthroplasty space across at least a portion of a base of the thumb metacarpal of a patient;
disposing said first anchor in the index metacarpal;
disposing said second anchor in the thumb metacarpal;
tensioning said second suture so as to draw said central section tightly across at least a portion of the base of the thumb metacarpal of a patient;
securing said second suture to said second anchor; and
repairing the portal.

2. The method according to claim 1 wherein at least one of said first suture and said second suture is a long lasting absorbable suture.

3. The method according to claim 1 wherein said central section has a configuration selected from the group consisting of quadrilateral, elliptical and polygonal.

4. The method according to claim 1 wherein the central section is made from a terminally sterile material.

5. The method according to claim 1 wherein said central section comprises biologic material.

6. The method according to claim 1 wherein said central section comprises porous material.

7. The method according to claim 1 wherein said central section comprises non-porous material.

8. The method according to claim 1 wherein the central section comprises a combination of materials including a long lasting absorbable weave.

9. The method according to claim 1 wherein the trapeziectomy is an entire trapeziectomy.

10. The method according to claim 1 wherein the portal is created by way of a Wagner incision.

11. The method according to claim 1 further comprising the step of performing a suture suspension arthroplasty just proximal to the implantable sling.

12. The method according to claim 1 further comprising forming a hole in the thumb metacarpal prior to disposing said second anchor in the thumb metacarpal.

13. The method according to claim 1 wherein the trapeziectomy is a partial trapeziectomy.

14. The method according to claim 1 wherein tensioning comprises drawing the central section towards the index metacarpal.

* * * * *